United States Patent [19]
Slomka et al.

[11] Patent Number: 5,109,714
[45] Date of Patent: May 5, 1992

[54] METHOD AND MEANS FOR DYNAMIC MEASUREMENT OF RATES OF ADSORPTION FROM SOLUTIONS

[75] Inventors: Bogdan J. Slomka; William H. Buttermore, both of Ames, Iowa

[73] Assignee: Iowa State University Research Foundation, Ames, Iowa

[21] Appl. No.: 410,473

[22] Filed: Sep. 21, 1989

[51] Int. Cl.$^5$ .................................... G01N 15/08
[52] U.S. Cl. ................................. 73/865.5; 73/38
[58] Field of Search ......................... 73/38, 865.5

[56] References Cited

U.S. PATENT DOCUMENTS

| | | | |
|---|---|---|---|
| 3,211,007 | 10/1965 | Atkins | 73/865.5 |
| 3,286,530 | 11/1966 | Ayers | 73/865.5 |
| 3,349,625 | 10/1967 | Benusa et al. | 73/865.5 |
| 3,482,452 | 12/1969 | Tabikh | 73/865.5 |
| 3,500,675 | 3/1970 | Sandstede et al. | 73/865.5 X |
| 3,555,912 | 1/1971 | Lowell | 73/865.5 |
| 3,884,083 | 5/1975 | Lowell | 73/865.5 |
| 3,969,242 | 7/1976 | Kruse | 210/25 |
| 4,067,959 | 1/1978 | Bolz | 424/1 |
| 4,270,925 | 6/1981 | Isa et al. | |
| 4,305,291 | 12/1981 | Nelson | 73/865.5 |
| 4,414,111 | 11/1983 | Iwaisako et al. | 210/500.2 |
| 4,645,689 | 2/1987 | Sjoquist | |
| 4,704,245 | 11/1987 | Asakura et al. | 376/245 |

FOREIGN PATENT DOCUMENTS

1349738  4/1974  United Kingdom ............... 73/865.5

Primary Examiner—Hezron E. Williams
Assistant Examiner—Joseph W. Roskos
Attorney, Agent, or Firm—Zarley, McKee, Thomte, Voorhees, & Sease

[57] ABSTRACT

A method and apparatus for dynamic measurement of rates of absorption from solutions. The method has the advantage of avoiding the use of solvent normally used to establish a baseline. The method involves pre-evacuating the adsorbent contained in an adsorbent cell and thereafter rapidly contacting the adsorbent with analytical solution, all without prior exposure of adsorbent to pure solvent. The result is a sharp characteristic adsorption line.

7 Claims, 2 Drawing Sheets

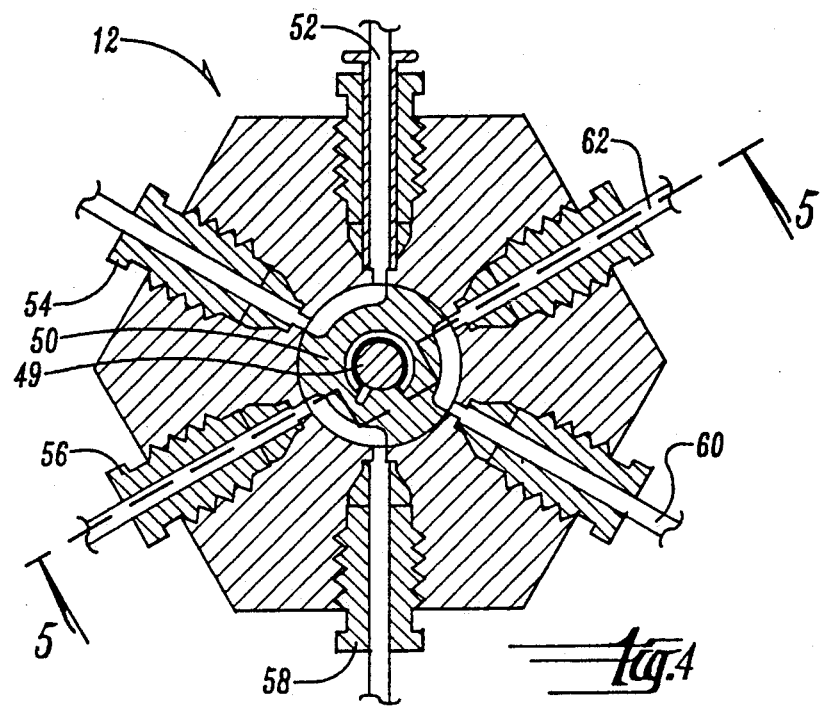
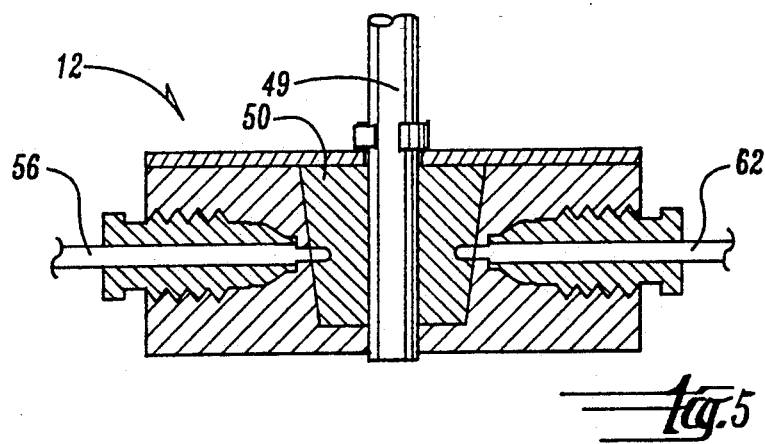

METHOD AND MEANS FOR DYNAMIC MEASUREMENT OF RATES OF ADSORPTION FROM SOLUTIONS

GRANT REFERENCE

This invention was made with Government support under Contract No. W-7405-ENG82 awarded by the Department of Energy. The Government has certain rights in the invention.

FIELD OF THE INVENTION

This invention relates to techniques for measurement of adsorption at solid/liquid interfaces and in particular, a means and method for dynamic measurement of rates of adsorption.

BACKGROUND OF THE INVENTION

Conventionally, adsorption of solutes on solids is measured in static systems (test tubes, vials, etc.) followed by spectrophotometric determination of solute concentration in the supernatant liquid. This type of procedure is specifically suited to studies of adsorption equilibria, determination of adsorption isotherms, and subsequent calculation of specific surface areas. Determination of adsorption rates in static systems, although possible, is a tedious and time consuming task.

Existing dynamic techniques for measurement of adsorption from solutions normally employ a fixed-bed of adsorbent sample contained in a column which is initially filled with solvent or a carrier liquid. An analytical solution is then passed through the column and the concentration of eluate is continuously measured, typically by a photometric detector. As used herein the term "analytical solution" refers to any fluid for which adsorption on the solid is to be measured. It includes gases and/or liquids.

Typically, existing procedures involve the use of two liquid-phase delivery circuits, one circuit for pure carrier liquid and the other for the analytical solution. In such systems, carrier liquid is first passed through a cell containing solid sample and then through a concentration detector to obtain a carrier liquid baseline, i.e., the recorded output signal for no solute (dissolved substance) present at the detector. As soon as the baseline is established for the carrier liquid, the flow is switched from carrier liquid to analytical solution which now passes through the adsorbent bed. The recorded detector response is a breakthrough curve representing the solute concentration change as seen at the detector throughout the time of adsorption. The rate of adsorption as a function of time must be corrected by making allowance for the adsorption on the components of the empty sample column. The correction is a similar trace resulting from repeating the entire procedure with an empty column.

In the conventional method, the analytical solution must displace the carrier liquid present in the column containing a sample of adsorbent in order to appear at the concentration detector. This displacement causes a change in concentration from zero (pure carrier liquid) to that of the analytical solution used. Consequently, as the carrier is being displaced by the analytical solution, adsorption occurs on sample particles from a liquid phase of gradually increasing solute concentration. The sharpness of this change in concentration will depend on how efficiently the carrier liquid is displaced. This effect will vary from one sample of adsorbent to another, subject to differing particle sizes, porosities of samples, void volume of the column, and other parameters affecting adsorptive and hydrodynamic characteristics of the sample bed, sample lines and other pathways from the sample to the detector. This displacement of carrier by analytical solution will occur differently in an empty sample column than in a column packed with solid particles, e.g., due to different internal volumes in each case. Resulting adsorption rate profiles will then bear some error attributable to this particular procedure. Another serious drawback of the conventional method is the necessity to frequently replace pure solvent by analytical solution and vice versa, in case of multiple measurements, e.g., when samples of different adsorbents must be measured consecutively.

Heretofore, it has been thought necessary to employ a solvent or carrier for a variety of reasons. Amongst those are the need to remove all gases from the system and to establish a baseline before analytical solution is used. Thus, the state of the art now normally used in measuring adsorption rates includes as an essential step flushing of the system with solvent carrier and detection of background rates. However, the problems inherent in this procedure are several fold. Normally, it is time consuming. It also provides for a lack of sharp and distinctive adsorption lines for the analytical solution. This is so because there is a gradual change from background solvent carrier to analytical solution and the operator is never quite sure where one ends and the other begins. This lack of a distinct sharp break line makes interpretation of results more difficult, in addition to being time consuming.

Nevertheless, as an analytical technique, adsorption characteristic measurements are useful in a variety of analytical applications including measurements of turbidity, light transmission, acidity, and the like. Some examples of practical applications for which they may be used include characterization of mineral and coal surfaces by adsorption of dyes, determination of surface areas, examining the accessibility of porous structures to dye molecules, and qualitative evaluation of active carbon, etc.

Accordingly, it can be seen that there is a real and continuing need for improvements in analytical techniques involving measurement of adsorption profiles of solids.

This invention has as a primary objective to provide a means and method for adequate contacting of adsorbent with analytical solution which avoids the need for use of carrier solvents and which allows for sharp, distinct adsorption profiles in dynamic systems.

Another objective of the present invention is to provide a system which accomplishes the above referred to primary objective in an economical and efficient manner.

A yet further objective of the present method and system is to develop a system that requires only one liquid phase delivery circuit.

An even further objective of the present invention is to develop a system which has no need for carrier solvent and thus avoids the need for time consuming rinsing of the system with pure solvent before and between measurements.

Another objective of the present invention is to provide an adsorbent system and/or cell which allow monitoring of adsorption rates as early as one second after start of the test.

An even further objective is to develop a dynamic system which provides adsorption profiles which can be more easily interpreted.

The method and manner of accomplishing each of the above objectives will be apparent from the detailed description of the invention which follows hereinafter.

BRIEF DESCRIPTION OF THE DRAWINGS

FIG. 4 shows a cross-section of a six-way port valve.

FIG. 5 shows a view of a six-way valve along line 5—5 of FIG. 4.

SUMMARY OF THE INVENTION

The invention relates to a method and system for dynamic measurement of rates of adsorption from analytical solutions. The system employs a fixed bed of adsorbent maintained in the static cell but connected to a six-port valve which allows it to be switched between the on and off-line modes. The method involves pre-evacuating fluids from adsorbent contained in a closed adsorption cell followed by rapidly contacting adsorbent in the cell with analytical solution, without prior exposure of adsorbent to carrier solvent.

DETAILED DESCRIPTION OF THE INVENTION

Figure 1:
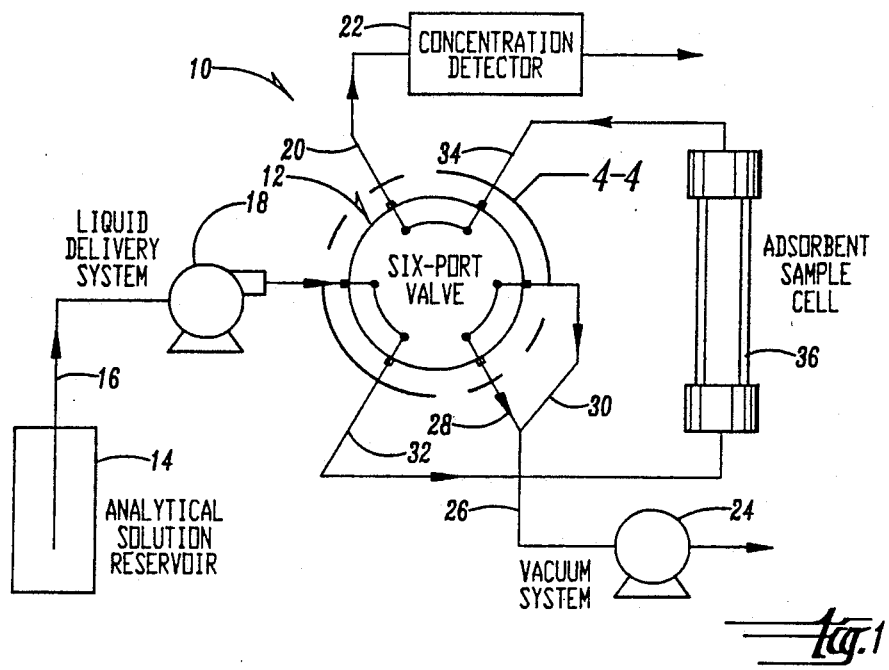
FIG. 1 shows a cell of the present invention used in a fixed bed adsorbent loop connected to a six-port valve in the on-line mode.
Figure 2:
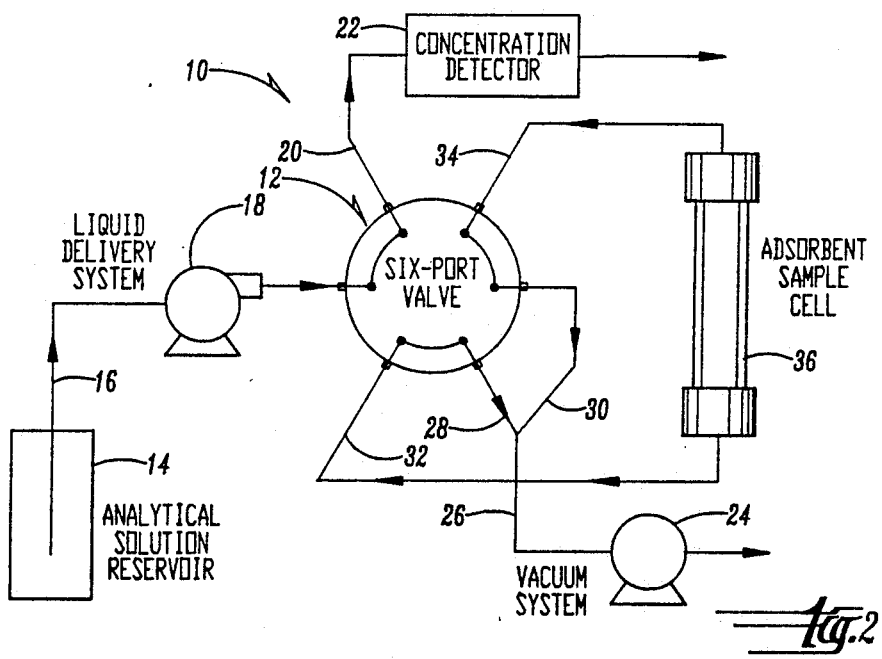
FIG. 2 shows the same system of FIG. 1 in an off-line mode.

FIGS. 1 and 2 show an enclosed loop system which may be used for practice of this invention. The closed loop system referred to generally as 10 employs a six-way valve 12 which is commercially available from companies such as Valco Instruments Company of Houston, Tex. It goes without saying that other valves which accomplish the same purpose of having the ability to selectively control different flow channels through them may be used. An analytical solution such as, for example, methylene blue dye is contained in solution reservoir 14 and can be pumped via line 16 and pump 18 into the six-port valve 12.

The system is shown in a pre-evacuation or off-line mode in FIG. 2. In this mode, analytical solution from reservoir 14 can be pumped via line 16 and pump 18 into six-port valve 12 wherein it is placed in communication with concentration detector 22 via line 20. Turning to the other side of the system, a vacuum pump 24 is in communication with six-port valve 12 and through the flow channels in that valve via lines 26, 28, 30, 32 and 34 with adsorbent sample cell 36. Thus, in the off-line mode the vacuum pump 24 can be turned on to evacuate adsorbent sample cell 36 of all contaminating fluids and pump 18 can be used to establish a detector base line for pure analytical solution.

FIG. 1 shows the system on-line or in operational mode. After the adsorbent sample cell 36 has been pre-evacuated, analytical liquid, such as methylene blue solution is pumped via pump 18 into six-port valve 12 and via line 32 into adsorbent sample cell 36, it passes through the sample 36, through line 34, into line 20 and from there to concentration detector 22. Thus analytical solution directly contacts the sample 38 without first using any carrier solvent. As a result, detector 22 provides for sharp and distinct and readings, without any "dilution" of the readings by a solvent carrier system.

Figure 3:
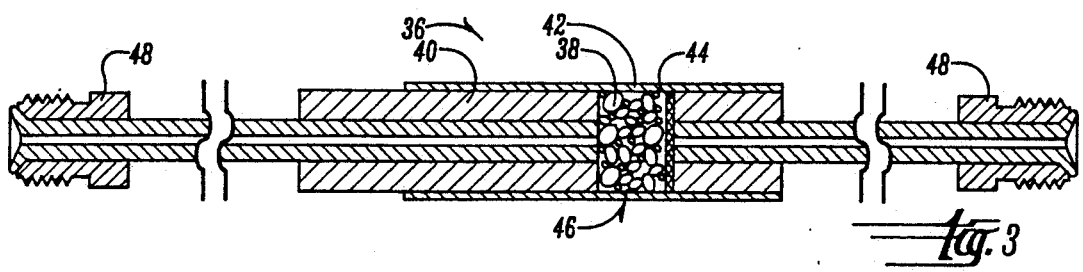
FIG. 3 shows a sectional view of a typical cell for use in this invention.

The cell 36 is shown in detail in FIGS. 3. As illustrated, it represents a closed receptacle. Typically, a satisfactory cell can be made from inert polymeric plastic materials such as Teflon ®. An inner tube 40 is inserted matingly into an exterior tube 42. Positioned in tube 42 is a fine frit or screen 44. The two tubes are moved towards each other such that there is a continuous communicating bore between the interiors of tube 40 and the tube 42. They define a sample chamber 46 which can be used to hold an adjustably sized sample 38. Caps 48 can be threaded onto the ports of six-way valve 12.

In the ideal case, the solid sample 38 should be constantly contacted with the flowing analytical solution while the change of in solution concentration is monitored continuously and recorded. The change in the solute concentration due to adsorption should be kept sufficiently small compared to the starting concentration level, so it can be safely assumed that the adsorption occurs at approximately constant solute concentration. This can be accomplished by routine adjustment of the operational parameters such as the quantity of the solid contacted with analytical solution, particle mean diameter and particle size distribution, concentration of the analytical solution, flow rate, etc.

While an adjustable six-port valve 12 is conventional, sectional views of the same are shown in FIG. 4 and 5. As seen in FIG. 5, a valve handle (not depicted) but connected to shaft 49 can be turned to move center plug 50 which is rotatably mounted in the six-port valve 12 to allow rotation of handle shaft 49 and plug 50 to provide selective communication with various parts 52, 54, 56, 58, 60 and 62. Thus, the pathways through six-port valve 12 are selectively adjustable.

The cell 36 containing a fixed bed of solid adsorbent 38 constitutes a loop connected to six-port valve 12 which allows it to be switched between the on- and the off-line mode. The off-line mode (FIG. 2) is used for pre-evacuation of the cell containing the sample of adsorbent, while the analytical solution by-passes the cell flowing directly to the concentration detector 22. A baseline for the solute concentration of the analytical solution is then recorded. The dual purpose for the pre-evacuation step is to prevent air bubbles from appearing at the concentration detector and to accelerate filling the sample cell with the analytical solution.

The system described here provides for fast contacting of adsorbent with analytical solution. It is accomplished by redirecting the flow of solution from the by-pass route (off-line mode, FIG. 2) to flow through the pre-evacuated sample cell (on-line mode, FIG. 1).

According to the new method, as soon as pre-evacuation is completed, the six-port valve 12 is switched to the on-line mode (FIG. 1) and the analytical solution is allowed to enter the cell 36 while maintaining the initially set flow rate at the pump 18. The analytical solution 14, enters the cell 36 from both ends driven by the liquid delivery system on one end of the sample cell and driven by atmospheric pressure acting on the liquid in the detector line, downstream from the detector on the other end of the cell as shown in FIG. 1. This procedure causes no measurable fluctuation in detector output, provided the exit line from detector 22 is open to atmospheric pressure and filled with the solution. During the short time of cell filling the solution in the line downstream from the detector 22 retracts by slightly less than the void space in the pre-evacuated cell 36. Because the concentration of the solution in this line is constant, the detector response also remains constant despite the momentary backflow. In any case, the momentary backflow can be eliminated through the installation of a one-way valve downstream of the detector. After cell filling is completed the direction of the flow becomes uniform throughout the entire path of flow including the sample cell 36. Likewise, the flowrate becomes equal to the initially set value. It has been demonstrated in laboratory tests that filling the adsorbent cell 36 can be accomplished within 1 second after switching the six-port valve 12.

The present method, by employing only the analytical solution as the liquid phase, eliminates the otherwise necessary step of displacement of solvent by the solution. The adverse effects associated with the use of pure solvent as a part of the method are thereby eliminated. At the same time, the new method significantly shortens the measurement cycle. Thus, the invention provides an improvement in the dynamic measurement procedure for monitoring rates of adsorption at solid/liquid interfaces.

The following are advantages which are direct results of the present invention:
 1. The design of the adsorption apparatus is simple, i.e., it requires only one liquid phase delivery circuit.
 2. The solution concentration level provides the baseline, not the solvent, therefore, the need for time-consuming rinsing of the system with pure solvent between multiple measurements is eliminated.
 3. Fast filling of the adsorbent cell 36 with analytical solution allows for monitoring adsorption rates as early as 1 second after the start of the test.
 4. The adsorption rate profiles are more easily interpreted. The baseline is straight and horizontal, instead of an s-shaped breakthrough-type curve. More importantly, the results are adsorption rate profiles for constant solute concentrations. These cannot be attained using conventional systems for dynamic measurement of adsorption from solutions.

The following example serves to illustrate but not limit the process of the present invention.

EXAMPLE

Non-buffered 64.0 mg./l aqueous solutions of methylene blue was prepared by drying the dye under nitrogen at 110° C. for 2 hours and dissolving in de-ionized distilled water.

A bulk sample of coal with a narrow range of particle size was obtained by dry-sieving Illinois No. 6 coal to obtain 330 $\mu m$ to 425 $\mu m$ coal particles. Test samples were then prepared by wet-sieving to remove undersize material from the particle surfaces. Samples of increasing mineral content were prepared by density separation of the wet-sieved particles using aqueous solutions of CsCl at several specific gravities between 1.30 and 1.80 g/cc. Mineral samples were ground using a mortar and pestle, and 330 $\mu m$ to 425 $\mu m$ particles were obtained by wet-sieving. Preliminary tests were performed to determine the applicability of the dynamic adsorption technique to fine particle sizes. Illinois No. 6 coal was pulverized and dry-sieved to obtain samples smaller than 150 $\mu m$ and 44 $\mu m$.

A continuous-flow apparatus as shown in FIG. 1 and 2 was used for dynamic measurements of adsorption from liquid phases on solids. In a typical experiment, a pre-weighed sample of coal 38 is placed in a sample cell 36 and fixed between two 0.5- $\mu m$ stainless steel frits 44. The sample cell 36 is then connected to a six-port switch valve 12 and evacuated (FIG. 2 mode) to remove air. The valve 12 is set initially to direct the solution of dye to by-pass the cell containing the sample, causing it to flow directly through the ultraviolet/visible detector 22 (Varian UV-50) (FIG. 2). As soon as a baseline is established for the dye solution, the flowing solution is directed through the sample of coal (FIG. 1 mode) to the UV/Vis detector 22. The adsorbance measured for the effluent leaving the sample cell is due only to dye not adsorbed by the coal sample 38. The apparent absorbance is recorded at a fixed wavelength as a function of time using an A/D converter at a sampling rate of 2 $sec^{-1}$. This dynamic method of adsorption measurement allowed for continuous replacement of the fluid phase in contact with the coal sample, which is not possible in a closed, static system. The rates of adsorption were continuously measured as a function of time, giving characteristic profiles of adsorption rate, while the total adsorbate uptakes were obtained by integration of the rate profiles over the time of adsorption. The detector 22 response to dye concentration was sharp and linear for the concentrations and wavelengths used in the experiments. The detector was operated in the visible range at 610 nm. Based on preliminary results, two flow rates of solutions were selected, 1 and 0.5 ml/minute, according to the sample size of the materials tested. Other flow rates could be selected, if desired.

To evaluate the adsorptive components of coal and mineral surfaces, coal samples of uniform particle size and increasing mineral content were analyzed. Total mineral content was determined by standard ash analysis. Samples with very low ash content were used to approximate a non-mineral coal surface. To evaluate specific mineral adsorptive characteristics, mineral samples of uniform particle size and composition were analyzed. Ground coal samples of different mean particle size were analyzed to determine the effect of particle surface area.

The methylene blue was preferentially adsorbed on the mineral surfaces and the curves were sharp, distinct and easily readable to correlate with mineral content.

What is claimed is:
 1. A method for dynamic measurement of rates of adsorption on solids from analytical solutions comprising:
   (a) placing a solid adsorbent in an enclosed cell;
   (b) pre-evacuating the solid adsorbent to remove contaminating fluids;
   (c) rapidly contacting the adsorbent in the cell with an analytical solution without prior exposure of adsorbent to pure solvent; and
   (d) detecting the amount of analytical solution adsorbed.
 2. The method of claim 1 wherein the adsorbent cell can be selectively connected in the system to be included or excluded from the path of flow of analytical solution.
 3. The method of claim 2 wherein the means of selective connection is a multi-way switch valve.
 4. The method of claim 1 wherein the analytical solution is a gas.
 5. The method of claim 1 wherein the analytical solution is a liquid.
 6. A fixed bed flow adsorption apparatus for dynamic measurement of adsorption rates comprising:
   an adsorbent cell for holding an adsorbant sample;

a delivery system for an analytical solution including means for defining the path of flow of an analytical solution to selectively vary the path from said system to said adsorbent cell and one or more detector; and a concentration detector in selective communication with said cell; and whereby adsorbent can be selectively directed to said adsorbent cell and said detector.

7. A cell for measurement of adsorption rates of analytical solutions, comprising:

a flexible polymeric plastic exterior transport tube having an inner end and an outer end;

a flexible polymeric plastic interior tube having an inner end and an outer end and being matingly inserted into said exterior tube so that a sample chamber is defined by the interior ends of each of said interior and exterior tubes;

a sample frit positioned in said sample chamber; and sample port fastening caps removably fastened to the outer ends of each of said exterior and interior transport tubes.

* * * * *